United States Patent
Te Vrugt et al.

(10) Patent No.: US 8,491,502 B2
(45) Date of Patent: Jul. 23, 2013

(54) SYSTEM FOR REHABILITATION AND/OR PHYSICAL THERAPY FOR THE TREATMENT OF NEUROMOTOR DISORDERS

(75) Inventors: Juergen Te Vrugt, Aachen (DE); Gerd Lanfermann, Aachen (DE); Richard Daniel Willmann, Siegburg (DE); Edwin Gerardus Johannus Maria Bongers, Roermond (NL)

(73) Assignee: Koninklijke Philips N.V., Eindhoven (NL)

( * ) Notice: Subject to any disclaimer, the term of this patent is extended or adjusted under 35 U.S.C. 154(b) by 980 days.

(21) Appl. No.: 12/530,631

(22) PCT Filed: Mar. 12, 2008

(86) PCT No.: PCT/IB2008/050886
§ 371 (c)(1),
(2), (4) Date: Sep. 10, 2009

(87) PCT Pub. No.: WO2008/114166
PCT Pub. Date: Sep. 25, 2008

(65) Prior Publication Data
US 2010/0105991 A1   Apr. 29, 2010

(30) Foreign Application Priority Data
Mar. 16, 2007 (EP) .................................... 07104334

(51) Int. Cl.
*A61B 5/00* (2006.01)
(52) U.S. Cl.
USPC ........................................................ 600/587

(58) Field of Classification Search
USPC ................................. 600/485, 490, 587, 595
See application file for complete search history.

(56) References Cited

U.S. PATENT DOCUMENTS

| 8,010,368 B2 * | 8/2011 | Yamaki .......................... 704/275 |
| 2002/0183647 A1 | 12/2002 | Gozani et al. |
| 2006/0088385 A1 | 4/2006 | Ford et al. |
| 2006/0135884 A1 | 6/2006 | Hack et al. |
| 2006/0184051 A1 | 8/2006 | Hempstead et al. |

FOREIGN PATENT DOCUMENTS

| WO | 0044278 A1 | 8/2000 |
| WO | 2005074791 A1 | 8/2005 |
| WO | 2005104945 A2 | 11/2005 |
| WO | 2008017974 A2 | 2/2008 |

OTHER PUBLICATIONS

Mundermann et al: "The Evolution of Methods for the Capture of Human Movement Leading to Markerless Motion Capture for Biomechanical Applications"; Journal of Neuroengineering and Rehabilitation 2006, 3:6, pp. 1-11.

* cited by examiner

*Primary Examiner* — Max Hindenburg

(57) ABSTRACT

A sensor docking unit for attaching and removing sensor or marker onto/from a user's limb includes a guiding portion and a limb localization unit having a detector to determine if an insertion of the user's limb into a pre-specified position within the sensor docking unit has been completed correctly. A sensor or marker mounting device includes at least one sensor or marker entity to enable at least semi-automatic attachment and/or removal of the at least one sensor or marker to/from the user's limb in a reproducible manner. The sensor or marker mounting device is activatable to start with an attachment and/or removal of the at least one sensor or marker when a correct insertion of the user's limb has been determined by the limb localization unit.

6 Claims, 2 Drawing Sheets

SYSTEM FOR REHABILITATION AND/OR PHYSICAL THERAPY FOR THE TREATMENT OF NEUROMOTOR DISORDERS

The present invention relates to a system for rehabilitation and/or physical therapy for the treatment of neuromotor disorders, such as a stroke. After a stroke patients often suffer from disturbances in movement coordination. These disturbances are the least well understood but often the most debilitating with respect to functional recovery following brain injury. These deficits in coordination are expressed in the form of abnormal muscle synergies and result in limited and stereotype movement patterns that are functionally disabling. The result of these constraints in muscle synergies is for example an abnormal coupling between shoulder abduction and elbow flexion in the arm, which significantly reduces a stroke survivor reaching space when he/she lifts up the weight of the impaired arm against gravity. Current neurotherapeutic approaches to mitigate these abnormal synergies have produced limited functional recovery. In the leg the expression of abnormal synergies results in coupling hip/knee extension with hip adduction. The result of this is a reduced ability of activating hip abductor muscles in the impaired leg during stance.

When traditional therapy is provided in a hospital or rehabilitation center, the patient is usually seen for half-hour face-to-face sessions, once or twice a day. This is decreased to once or twice a week in outpatient therapy.

Current studies indicate that motor exercising for improving the coordination of the patient can be done at home as part of a tele-rehabilitation solution. If the exercising should be reviewed by a therapist technical solutions for unsupervised home stroke rehabilitation often require the use of markers or sensors for acquiring the patient's posture during exercises. Posture acquisition by inertial sensors or vision systems, which may require the placement of markers on the patient's body, are an attractive option.

A very attractive sensor solution is using cameras which view 2D or 3D coordinates of limbs and joints in space, depending on whether a single or multi camera system is used. However, acquiring limb position from a camera position requires finding and tracking of limbs in the image, which is a non-trivial task and an unsolved problem today, if no markers are used (see e.g. "the evolution of methods for the capture of human movement leading markerless motion capture for bio medical applications", e.g. Mundermann et al., J. Neuro Engineering and Rehabilitation 2006, 3:6).

In another monitoring system markers or inertial sensors are placed on a user's limb or on the body of the user to measure orientations in space or relative changes of position of the user's limbs in space and to compare the movements following predetermined exercises to a reference template. The tracking of marker positions by cameras in both the optical range and in the infrared is very reliable. In this area, commercial products exist.

The problem with such an approach is that existing marker-based tracking systems assume the user to be skilled enough to place the markers or sensors at exactly reproducible places; thus consistent results should be achieved. This assumption becomes unrealistic, if the user is a stroke victim. Instead, the exact position of the markers on the limbs will differ from one use to the other, since the user is not able to fix the marker or sensor in exactly the same position because of a loss of control of the movement of his arms hands and/or fingers if he is able to fix the sensors at all.

It is therefore an object of the present invention to provide a device which makes the handling of the sensors or markers easier and allows an accurate positioning of the sensors or markers on a patient's limbs or body.

This object is solved by a sensor docking unit for attaching and/or removing at least one sensor or marker entity onto/from a user's body in particular his limb(s) comprising a guiding portion to facilitate an insertion of at least one limb to be equipped with at least one sensor or marker into the sensor docking unit by guiding the limb into a pre-specified position, a limb localization unit comprising at least one detecting means to determine if the insertion of the user's limb into the pre-specified position within the sensor docking unit has been completed correctly and a sensor or marker mounting means including at least one sensor or marker entity to enable an at least semi-automatic attachment and/or removal of at least one sensor or marker onto/from the user's limb or the support of the manual attachment/removal process of sensors in a reproducible manner wherein the sensor or marker mounting means is activatable to start with an attachment and/or removal of at least one sensor or marker when a correct insertion of the user's limb has been detected by the detecting means.

With other words the invention discloses a system to place and remove sensors or markers on limbs of patients at exact and reproducible locations after the user has managed to place his limbs in a pre-specified position. While the user's limb is inserted into the unit, the correct positioning of the limb is continuously checked. Only if the limb has reached its position within the docking unit properly the sensors or markers may be manually, semi-automatically or automatically attached or removed to or from the user's limb. With this system it is possible for the user to perform exercises on his own responsibility without the need that the placement or removal of the sensors or the markers has to be supervised by specialized staff.

The sensor docking unit according to the invention attaches some or all sensors or markers on the body of the user required for a reliable monitoring of an exercise to be executed before the exercise session begins and detaches the sensors again after the conduction of the exercises if desired. Because of the pre-specified position of the patient's limb within the sensor docking station a reliable and reproducible positioning of the sensors or markers on exactly the same position as in the previous sessions is guaranteed and therefore a comparison of the movements being monitored for example by a camera or another monitoring means such as inertial sensors is very precise and with this facts such as the progress of the mobility of the user between two exercise sessions can be analyzed very precisely. Moreover a calibration of sensors can be made in that the sensor docking unit is used to attach a posture sensor on a segment of the user's body wherein the knowledge of the posture forced by the docking unit may be used to provide a means to compensate for misalignments of the sensor on the user's body that might occur even though the sensor docking unit was used to attach the sensors.

In one embodiment of the present invention the sensor docking unit comprises an activation means for activating the sensor or marker mounting means to start the sensor or marker mounting procedure. The activation means may include a receiver for receiving an acoustic signal and/or an impulse signal wherein upon reception of an acoustic signal or an impulse signal the mounting procedure of a sensor or marker entity may be initiated. The mounting process of the sensor or marker entities may be either triggered and performed manually or (semi-) automatically. An example of a manual trigger is a button or a switch on the sensor docking unit which may be pressed by the user and an acoustic signal may be a voice command given by the patient and processed by the system, equipped with means to actually let the sensor docking unit start the mounting of the sensors or markers.

Alternatively, the mounting process starts automatically when the body part to be equipped with sensors or markers has reached the correct position in the sensor docking unit. In the semi-automatic case the sensor docking unit may recognize that the body part has reached a certain position but requires confirmation from the patient before it starts the mounting process. This confirmation may be effected for example by giving a voice command or by pressing a certain button or switch. The docking unit may therefore generate a signal to indicate the user that the limb positioning has been completed correctly. This signal may be an acoustic signal, a light signal or an impulse signal.

Since the sensors form an independent entity as soon they are fastened to a user's body and thus are disengaged from the sensor docking unit they may need their own power supply. Therefore, in one embodiment, the sensor docking unit comprises a means to charge at least one sensor or sensor entity such as a battery charger or a charging set recharging the sensors or sensor entities while they are inserted in and coupled with the sensor docking unit.

The marker entity may comprise a spray mechanism to place markers at certain portions on a user's limb by spraying paint such as an ultra violet paint onto the user's body which can be detected by an appropriate camera system and can be easily washed away after the exercises have been completed. The process to remove the marker may also be supported by the sensor docking unit.

In a further embodiment of the present invention the sensor docking unit further comprises a data processor to update the software of for example the operating system of the sensors or marker entities and to exchange data being stored in the nodes of the sensor or marker entities. With this it may be possible to upload data required to properly operate the sensor, e.g. firmware, calibration data etc. for example to ease the maintenance of the sensors or markers or data regarding the mounting process such as fastening the sensor by closing a latch of a fastening belt being included in the sensor entity or in case of a marker entity the duration or quantity of the activation of a spray nozzle of the marker entity. On the other hand data being collected during the exercises that was temporarily stored on the sensor nodes may be downloaded to the data processor of sensor docking unit and afterwards may be transferred to a central processing unit.

The sensor docking unit may constitute a separate device, a collection of devices or may be integrated in a rehabilitation system. The rehabilitation system may comprise at least one sensor docking unit wherein each sensor docking unit in turn may be connected to a control unit to separately or simultaneously control the attachment or removal of the sensors or markers by the sensor or marker entities included in the sensor docking units, the docking unit being adapted for certain mounting positions like lower arm right or upper leg left.

In aforesaid rehabilitation system the control unit may be formed as an integral part of the sensor docking unit or may be formed as a separate unit. In case it is formed as a separate unit the communication between the sensor docking unit and the control unit may be conducted wireless for example by a Bluetooth or an optical infrared communication.

It may be advantageous if a control unit being either integrated or being formed as a separate part of a rehabilitation system may comprise voice recognition means to process a user's voice command. In case the control unit is formed as a separate part the sensor docking unit being connected to a user's limb can be made very light so that a handling is more comfortable for the user.

In one embodiment the sensor docking unit may include a locking means which disables the sensor or marker mounting means until the detecting means detects a correct insertion of the user's limb. With this an inevitable attachment of the sensor or marker entity aroused because of an accidentally pushing of the activations button or turning of the activating switch or vocal command is prevented.

A sensor docking unit, which meets the abovementioned object and provides other beneficial features in accordance with the presently preferred exemplary embodiment of the present invention will be described below with reference to FIGS. 1 to 3.

Those familiar with the state-of-the-art will readily appreciate that the description given herein with respect to those figures is for explanatory purposes only and is not intended to limit the scope of the invention.

Although in the present application in the following description reference is made to a user's arm, it is contemplated that other parts of the body parts, especially the limbs may also be equipped with sensors or markers in the same way.

Figure 1:
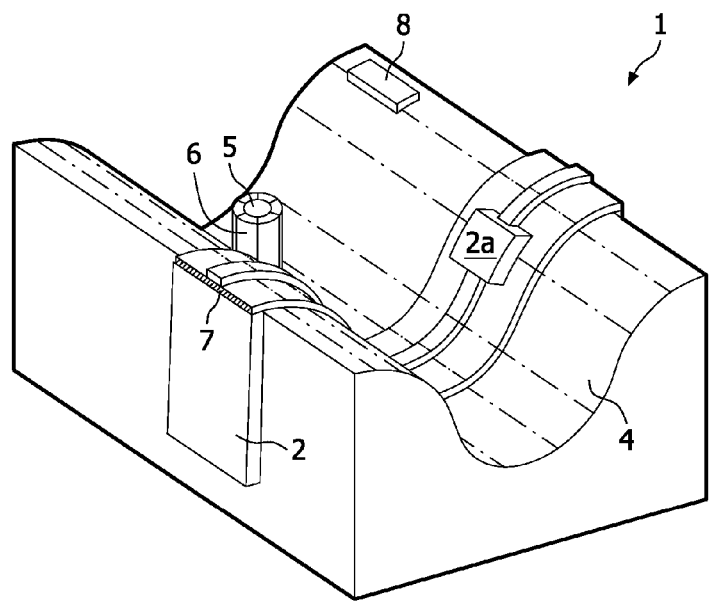
FIG. 1 shows a perspective view of a sensor docking station to be used to equip a forearm with sensors or markers according to the invention.
Figure 2:
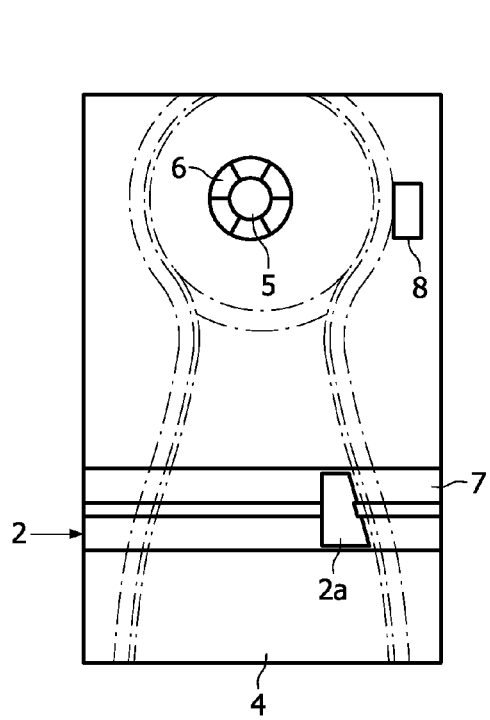
FIG. 2 shows a top view of a sensor docking unit according to FIG. 1.
Figure 3:
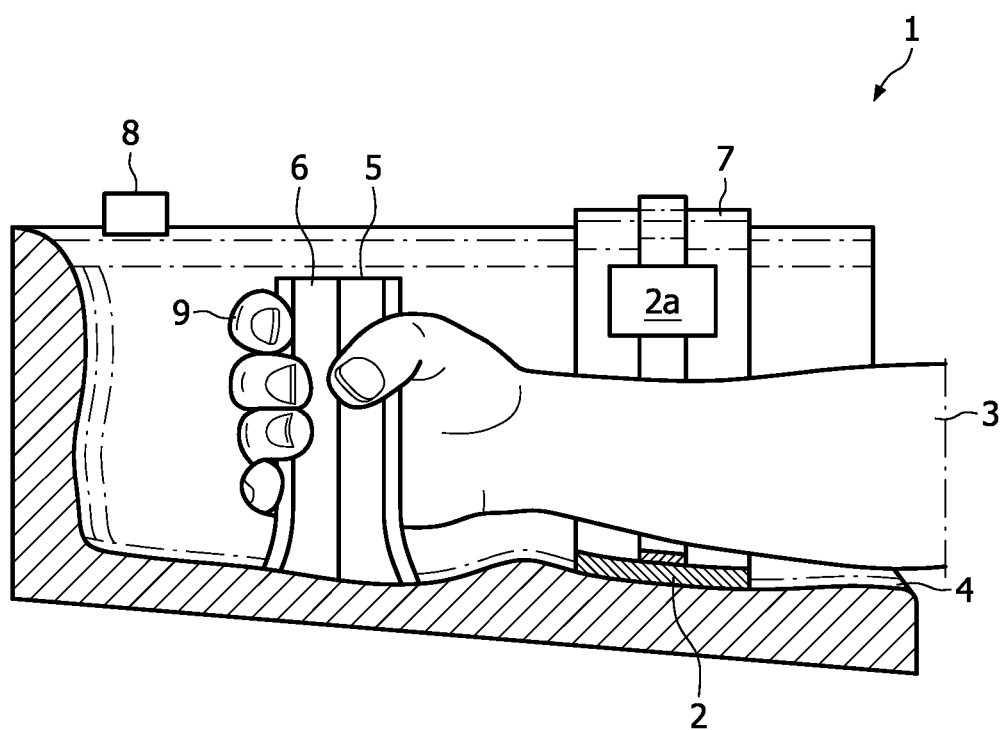
FIG. 3 shows a longitudinal section through the sensor docking station according to FIG. 1 schematically depicting a user's arm being placed in a pre-specified position.

FIG. 1 shows a schematic view of a sensor docking unit 1 for attaching and/or removing at least one sensor 2a or marker onto/from a user's limb 3. As also can be seen in FIG. 2 the sensor docking unit 1 has a guiding portion 4 to facilitate an insertion of a user's arm 3 to be equipped with sensors or markers 2a into the sensor docking unit 1 by guiding the arm 3 into a pre-specified position.

To detect, whether the insertion of the user's forearm 3 into the pre-specified position within the sensor docking unit 1 has been completed correctly the sensor docking unit 1 comprises a limb localization unit here in form of a pin 5 which is surrounded by tactile sensors building the detecting means 6 to detect the correct positioning of the user's forearm 3 in the sensor docking unit 1. The sensor docking unit 1 according to the invention furthermore includes a sensor or marker mounting means 7. In this embodiment the sensor or marker mounting means 7 includes one sensor entity 2 to conduct a semi-automatic attachment and removal of the sensor 2a onto and from the user's forearm 3 in a reproducible manner.

In one embodiment of the present invention (not shown) the sensor docking unit 1 is adaptable to the length of the user's arm 3 or its posture due to illness for example by shifting the pin 5 within the sensor docking unit 1 or by using a flexible material in the area of the guiding portion.

The sensor docking unit 1 further comprises a switch 8, which can be activated by the user by turning it over after the limb localization unit 5 signalized that the forearm 3 and the fingers 9 have been positioned within the sensor docking unit 1 correctly to activate the sensor mounting means 7 to start with the attachment of the sensor 2a. In this case, the correct position is reached as soon as the pin 5 is nearly completely surrounded by the user's fingers 9.

In this embodiment the mounting process starts automatically when the user's forearm 3 and fingers 9 have reached the pre-specified position in the sensor docking unit 1 and the limb localization unit 5 has detected the correct positioning of the user's forearm 3 and fingers 9.

Alternatively the sensor docking unit 1 may request a confirmation from the user or patient to start the mounting process after it has recognized that the forearm 3 and the fingers 9 have reached the limb localization unit 5 correctly. This is advantageous because the patient through all time maintains master of the situation and can decide on his own at which time the mounting process should be started and doesn't feel patronized by the sensor docking unit 1.

If the mounting process of the sensor or marker mounting unit 7 is conducted completely automatically, the sensor entity 2 is equipped with a fixation unit such as straps, clamps, sticky tape or other fastening means known in the state of the art (not shown in detail) included in the sensor entity 2 which is operated by the sensor mounting unit 7. This includes an appropriate closure of the fixation unit, for example by closing a latch of a fastening belt included in the sensor entity 2, if required.

In an further alternative embodiment of the present invention instead of the mechanical sensor entities 2, the sensor docking unit comprises a marker entity such as a marker application means to coat the user's limb with none-mechanical sensor entities such as markers. For example the marker application means such as dispensers print markers of a certain shape at a certain positions on the user's body or clothing using marker spray.

In one embodiment this marker spray reflects infrared light. A video camera combined with an infrared light source together with an appropriate means to post process the recorded data uses the markers to compute the posture of the parts of the body that contain the markers. The printed marker pattern may heavily support the identification of certain parts of the body and may be sufficient to conduct a precise analysis of the user's movements. After execution of the exercises theses markers may be removed simply by washing.

In the sensor docking unit 1 according to this embodiment of the present invention, a means to charge at least one sensor or marker entity 2 such as a battery charger or a charging set recharging the sensors 2a is integrated so that the sensors 2a can be recharged in case they are inserted in and coupled with the sensor docking unit 1. This is advantageous since the sensors 2a may form independent entities as soon as they are fastened to the user's forearm 3 and therefore need their own power supply as long as they are disengaged from the sensor docking unit 1.

According to a further embodiment, the sensor docking unit 1 comprises a data processor (not shown) to upgrade the software of the sensor or marker entities to exchange data being stored in the sensor or marker entity 2 including data for example regarding the mounting process such as fastening the sensor by closing a latch of a fastening belt being included in the sensor entity or in case of a marker entity the duration or quantity of the activation of a spray nozzle of the marker entity or on the user's side the duration of the exercises a user accomplishes data to ease a maintenance of the sensors. The data processor may also be integrated into the sensor docking unit 1.

With the above, the sensor docking unit 1 supports a user or patient in attaching and removing sensors 2a in particular on his limbs, allows a reproducible positioning of the sensors or markers 2a, provides the basis for a well-defined initial positioning of the sensors or markers 2a and might support a calibration of sensors 2a and to ease maintenance of the sensors 2a by for example charging the batteries of the sensors 2a and/or providing the possibility of updating software like the operating system/firmware or calibration data in the sensors 2a.

The sensor docking unit 1 may be connected to a control unit which together build up the rehabilitation system. Alternatively, the control unit may be integrated in the sensor docking unit 1. Of course it is also possible to attach multiple sensor entities 2 handled by a single sensor docking unit 1.

The method of mounting of the sensors or markers 2a onto the user's limbs 3 works as follows:

First of all the user is invited to insert his left or right forearm to be equipped with the sensor or marker entity 2 into the guiding portion 4 of the sensor docking unit to guide the arm 3 into a pre-specified position which enables a mechanical reproducible orientation of the arm 3 while mounting the sensors or markers 2a. The arm 3 of the user has to be inserted into the sensor docking unit 1 until the user's arm 3 has reached the pre-specified position within the sensor docking unit 1 completely and correctly. As soon as the tactile sensors on the pin 5 building the detecting means 6 detect the user's arm 3 and fingers 9 to be inserted in the right position a signal is generated by the sensor docking unit 1 indicating the accomplishment of the insertion. The signal is forwarded to the sensor mounting means 8 to start the sensor or marker mounting process which can be triggered either manually or (semi-) automatically. In this embodiment the mounting process starts automatically when the user's limb has reached a certain position in the sensor docking unit 1 and the limb localization means 5 has generated a signal indicating that this position has been reached by the user's arm 3 and fingers 9. In the semi-automatic case the sensor docking station recognizes that the user's body part has reached a certain position and requests a confirmation from the user that the mounting process should be initiated.

In an alternative of the present invention the patient is informed by the sensor docking unit 1 for example by means of an acoustic signal, that the correct position has been reached and that he now may give a voice command or press a start button 10 to start the mounting procedure of the sensor entities 2. The acoustic signal may also be substituted by an impulse signal such as vibration.

To mount the sensors or markers 2a on the user's body or limb 3, it is equipped with a fixation unit (not shown). During the mounting process, the sensor docking unit 1 automatically operates the fixation unit for attachment and removal of the sensor entity 2. This includes an appropriate closure or opening of the fixation unit if required, for example a latch of a fastening belt on which a sensor 2a is fixed. After attaching the sensors 2a to the users body part 3 they can be calibrated because of their pre-specified placement relative to the user's body.

Besides mechanical sensor entities 2 the sensor docking unit 1 can be deployed to coat none-mechanical sensors such as markers onto certain body parts of the user. For example the sensor docking unit 1 can be used to print markers of certain shape at a certain position on the body or clothing of the user using marker spray. In one embodiment this marker spray reflects infrared light. A video camera combined with an infrared source together with an appropriate means to post process data uses the markers to compute the posture of the parts of the body that contain the markers. The printed marker pattern may heavily support the identification of certain parts of the body and their movement during an exercise.

The invention claimed is:

1. A sensor docking unit for attaching a sensor to a limb of a user comprising:

a guiding portion configured to facilitate insertion of the limb into the sensor docking unit by guiding the limb into a predetermined position;

a limb localization unit located in the guiding portion and comprising a detector configured to determine whether the limb is located at the predetermined position, wherein the limb localization unit is configured to generate a signal when the limb is located at the predetermined position; and a sensor mounting device including a sensor and configuring to enable attachment of the sensor to the limb in response to the signal.

2. The sensor docking unit according to claim 1, further comprising an activator configured to activate the sensor mounting to device in response to activation by the user when the signal is generated.

3. The sensor docking unit according to claim 2, wherein the activation by the user includes one of pressing a button and issuing a voice command.

4. The sensor docking unit according to claim 1, wherein a length of the guiding portion is adaptable to a length of the limb of the arm by shifting a location of the limb localization unit in the guiding portion.

5. A method for attaching a sensor to a limb of a user comprising the act of:

inserting the limb into a guiding portion of a sensor docking unit until a predetermined position;

detecting by a detector that the limb reached the predetermined position;

generating a signal in response to the detecting act;

in response to the generating act, enabling activation of a sensor mounting device including a sensor and configured to attach the sensor to the limb; and removing the user's limb out of the sensor docking unit.

6. The method of claim 5, further comprising the act of activating the sensor mounting device in response to one of pressing a button and issuing a voice command by the user in presence of the signal.

* * * * *